(12) United States Patent
Haener et al.

(10) Patent No.: US 7,862,698 B2
(45) Date of Patent: Jan. 4, 2011

(54) DEVICE AND METHOD FOR PREPARING AN ELECTROCHEMICAL SENSOR

(75) Inventors: Paul Haener, Arlesheim (CH); Joseph Lang, Ranspach le Haut (FR)

(73) Assignee: Sentec AG, Therwil (CH)

( * ) Notice: Subject to any disclaimer, the term of this patent is extended or adjusted under 35 U.S.C. 154(b) by 874 days.

(21) Appl. No.: 10/509,227

(22) PCT Filed: Aug. 6, 2002

(86) PCT No.: PCT/CH02/00431
§ 371 (c)(1),
(2), (4) Date: Sep. 24, 2004

(87) PCT Pub. No.: WO2004/013624
PCT Pub. Date: Feb. 12, 2004

(65) Prior Publication Data
US 2005/0120542 A1 Jun. 9, 2005

(51) Int. Cl.
*G01N 27/26* (2006.01)
(52) U.S. Cl. ............... 204/433; 205/786; 204/194; 29/592.1
(58) Field of Classification Search .......... 204/705, 204/402; 303/22.7; 222/207
See application file for complete search history.

(56) References Cited

U.S. PATENT DOCUMENTS 3,946,599 A * 3/1976 Patt ..................... 73/644
4,285,792 A * 8/1981 McGandy ............... 204/402
4,325,797 A * 4/1982 Hale et al. .............. 204/415
4,502,213 A * 3/1985 Madden et al. ............ 29/730
4,738,765 A * 4/1988 Cortina et al. ............ 204/415
4,830,713 A 5/1989 Gagescu
5,776,330 A * 7/1998 D'Muhala .............. 205/687

FOREIGN PATENT DOCUMENTS

DE 2753698 A1 6/1979
DE 4232909 A1 4/1994
EP 0267978 A1 11/1986

OTHER PUBLICATIONS

Glasspool, W., et al: "A screen-printed amperometric dissolved oxygen sensor utilizing an immobilized electrolyte gel and membrane." Sensors and Actuators B, Elsevier Sequoia S.A., Lausanne, CH, Bd. 48, Nr. 1-3, 30. May 30, 1998, Seiten 308-317, XP004147357.
Clark, J., et al: "Noninvasive Assessment of Blood Gases." AM Rev Respir Dis 1992; 145:220-232.
PCT Search Report for Patent Application 2004/013624. Dec. 3, 2002.

* cited by examiner

*Primary Examiner*—Stephen Rosasco
*Assistant Examiner*—Rashid Alam
(74) *Attorney, Agent, or Firm*—Pearl Cohen Zedek Latzer, LLP

(57) ABSTRACT

A device and method for preparing an electrochemical sensor may enable the sensor head thereof to be provided with an electrolyte and a membrane. The device may include a retaining means for the sensor in addition to means for depositing the electrolyte and means for depositing the membrane.

23 Claims, 5 Drawing Sheets

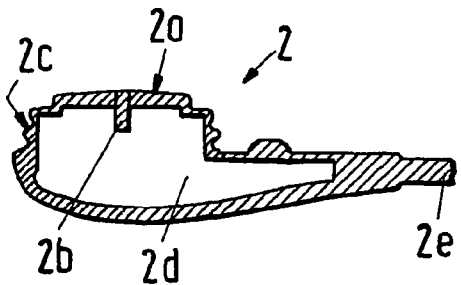
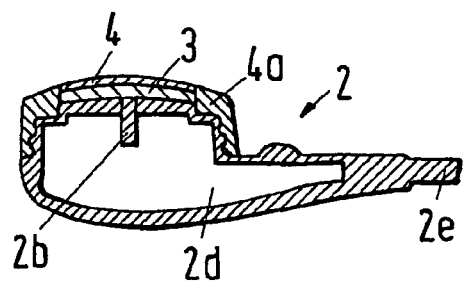
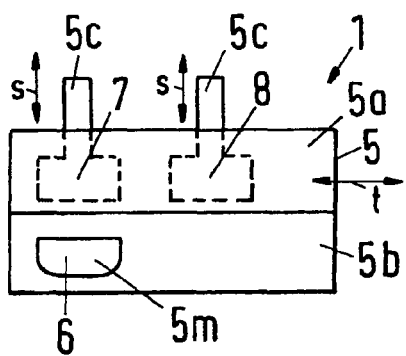
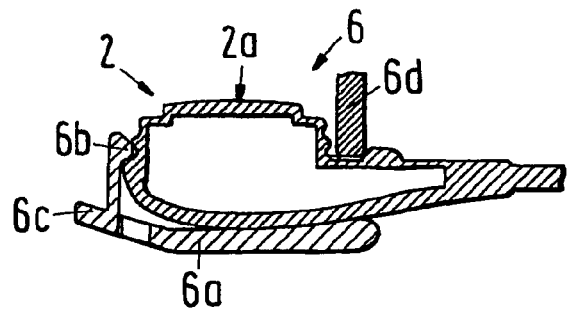
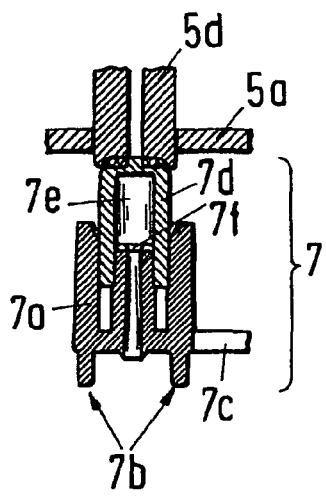
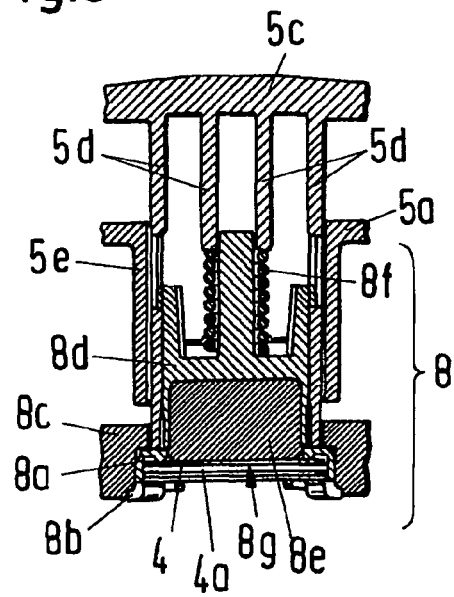

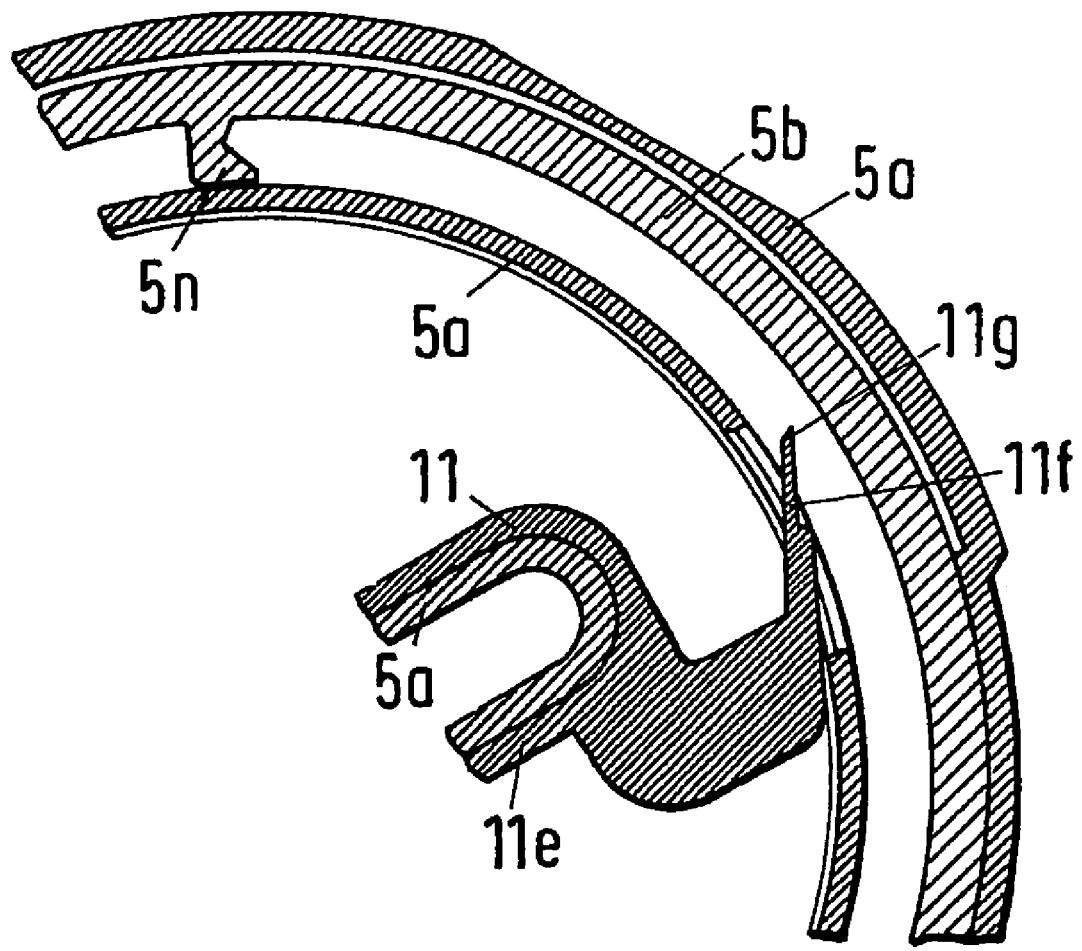

US 7,862,698 B2

DEVICE AND METHOD FOR PREPARING AN ELECTROCHEMICAL SENSOR

PRIOR APPLICATION DATA

The present application is a national phase application of International Application PCT/CH2002/000431, entitled "DEVICE AND METHOD TO PREPARE ELECTROCHEMICAL SENSORS" filed on Aug. 6, 2002, incorporated by reference in its entirety.

FIELD OF THE INVENTION

The invention relates to an apparatus for the preparation of an electrochemical sensor.

BACKGROUND OF THE INVENTION

Electrochemical sensors are known, the measuring principle of which is based on ion diffusion. This ion diffusion takes place, using a suitable electrolyte, usually via a semi-permeable membrane, for example a glass for $H^+$ and Teflon for $CO_2$. Such electrochemical sensors enable primarily the $H^+$-concentration to be measured and indirectly, via the measurement of the $H^+$-concentration, also the concentration of, for example, $CO_2$ or $O_2$ to be determined. The measurement of the $H^+$-concentration takes place with a pH electrode, also termed a glass electrode.

A modification of the pH electrode is the $pO_2$ electrode, also termed a Clark electrode, which serves for the measurement of the $O_2$ concentration.

A further modification of the pH electrode is the $pCO_2$ electrode also termed a Severinghaus electrode which permits the measurement of the $CO_2$ concentration. In the Severinghaus electrode the $CO_2$ diffuses through a membrane (Teflon) into an electrolyte with an $NaHCO_3$ solution with: $CO_2 + H_2O <-> H_2CO_3 <-> H^+ + HCO_3$ applying. The $H^+$-concentration is measured with the pH electrode and the $CO_2$ value derived therefrom.

Such electrochemical sensors are used amongst other things for the measurement of blood gas values such as the $CO_2$ concentration or the $O_2$ concentration in the blood. The electrochemical sensor is applied to a position of the human body with a good circulation of blood in order to measure the transcutaneous carbon dioxide partial pressure ($tCpCO_2$) or the transcutaneous oxygen partial pressure ($tcpO_2$). Extensive information concerning these generally known measurement methods are for example to be found in the following review article "Noninvasive Assessment of Blood Gases, State of the Art" by J. S. Clark et al., Am. Rev. Resp. Dis., Vol. 145, 1992, pp 220-232.

It is also known to provide the electrochemical sensor with additional sensors, for example with LEDs and photoelectric sensors in order to simultaneously carry out a pulsoximetric measurement. A combination sensor of this kind for the combined measurement of the oxygen saturation of the haemoglobin in arterial blood and also of the arterial carbon dioxide partial pressure is known from the document EP 0 267 978 A1. This combination sensor includes as an electrochemical sensor, a Severinghaus electrode for the measurement of the transcutaneous $CO_2$ partial pressure and also an arrangement for the measurement of the oxygen saturation ($SpO_2$) by means of pulsoximetry.

A disadvantage of electrochemical sensors is the fact that their preparation and maintenance is very demanding and requires trained specialist personal. For the Severinghaus electrode the semi-permeable membrane and the electrolyte which is located between the membrane and the sensor head must, for example, be regularly exchanged in order to ensure a problem-free operation. This servicing work is very demanding because the measurement accuracy is dependent on the thickness of electrolyte layer and also on the precise arrangement of the membrane. The reproducability of the measurement accuracy is of central importance, because vital parameters, such as the $CO_2$ content in blood are measured with the electrochemical sensor. A faulty measurement of this parameter could prove lethal for a patient. The electrochemical sensor is, moreover, frequently used in a hectic environment, such as in an intensive care station in the hospital. The electrochemical sensor is however also increasingly frequently used in the home area (home care) in order to monitor patients at home.

SUMMARY OF THE INVENTION

It is thus the object of the present invention to design the preparation of the electrochemical sensor reliably and simply.

The invention is in particular solved with an apparatus for the preparation of an electrochemical sensor in order to provide its sensor head with electrolyte and a membrane comprising a holding means for the sensor, a means for the dispensing of the electrolyte and also a means for the dispensing of the membrane.

The holding means, the means for the dispensing of the electrolyte and also the means for the dispensing of the membrane are jointly arranged in the same apparatus, which has the advantage that the sensor head can be reproducibly and very precisely provided with the electrolyte and also equipped with the membrane. The apparatus is preferably designed such that the sequence of preparation of this sensor is compulsorily guided in that first the electrolyte is dispensed and thereafter the sensor head can be equipped with the membrane.

The holding means, the means for the dispensing of the electrolyte and also the means for the dispensing of the membrane are advantageously arranged within a common housing, so that they are not accessible from the outside during the preparation of the sensor.

The means for the dispensing of the membrane and for the placement of the same of the sensor head preferably has a spring which is arranged such that the membrane is dispensed with a reproducible pressing force onto the sensor head and secured to it. Moreover, the means for the dispensing of the membrane advantageously has a pressing body with a pressing surface which, during the dispensing of the membrane, arealy contacts the membrane in order to reproducibly displace the electrolyte located between the membrane and the sensor head in such a way that the sensor connected to the membrane has a reproducible layer thickness of electrolyte, in particular a uniform layer thickness of electrolyte, between the sensor head and the membrane. This apparatus has the decisive advantage that every sensor equipped with the membrane has an essentially identical layer thickness of electrolyte. This increases the measurement reliability and reduces faulty measurements. The apparatus of the invention has the advantage that the preparation of the electrochemical sensor is essentially determined by the characteristics of the apparatus and no longer by the experience and ability of a specialist. Thus, even in a stress situation, such as, for example, results at an intensive care station, a reliable preparation of the electrochemical sensor is ensured. Moreover, it is also possible for an inexperienced person to reliably prepare the sensor, for example in the home area.

The apparatus of the invention also has, in a preferred embodiment, a means for cleaning the sensor head and also a means for the removal of an old membrane. An already used sensor can thus be put into the apparatus of the invention, wherein, with compulsory guidance the old membrane is first removed from the sensor, thereafter the sensor head is cleaned, the sensor head is provided with electrolyte and finally the sensor is provided with a new membrane.

In an advantageous design all consumed parts which are required for the preparation of the electrochemical sensor are arranged in a common carrier, with this carrier being designed as an exchangeable part preferably as a disposable or throw-away part. In this connection, prior to each preparation of an electrochemical sensor a new common carrier is first to be laid into the apparatus of the invention.

It is however also possible to conceive the entire apparatus of the invention as a disposable part or throw-away part so that no common carrier has to be exchanged. This apparatus contains all the means required for the preparation of an electrochemical sensor and does not therefore have to be opened. This apparatus is thus particularly simple to operate.

DESCRIPTION OF THE DRAWINGS

The invention will be described with reference to embodiments. There are shown:

FIG. 1a a longitudinal section through an electrochemical sensor without a membrane set in place;

FIG. 1b a longitudinal section through an electrochemical sensor with a membrane set in place;

FIG. 2 a side view of a schematically represented apparatus for the preparation of an electrochemical sensor;

FIG. 3 a longitudinal section through a sensor held in a holding means;

FIG. 4 a longitudinal section through a means for the dispensing of the electrolyte;

FIG. 5 a longitudinal section through a means for the dispensing of the membrane;

FIG. 15 a partial view of the section along the section line A-A of FIG. 11.

In the following the same reference numerals will be used for the same items.

DETAILED DESCRIPTION OF THE INVENTION

Figure 6:
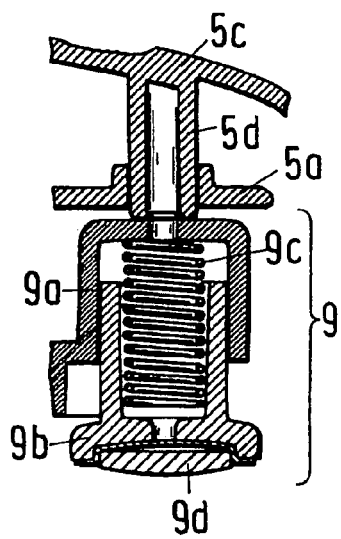
FIG. 6 a longitudinal section through a means for the cleaning of the sensor head.

FIG. 1a shows in a longitudinal section an electrochemical sensor 2 with a sensor head 2a, glass electrode 2b, holding grooves 2c, inner space 2d and cable 2e. The components located in the interior of the sensor 2 are not shown. FIG. 1b shows in a longitudinal section the sensor 2 illustrated in FIG. 1a which is prepared for the measurement in that its sensor head 2a is now covered with an electrolyte 3 and a membrane 4 with a holding ring 4a is secured to its sensor head 2a. The electrochemical sensor shown in FIG. 1b could for example contain a Clark electrode or a Severinghaus electrode.

FIG. 2 shows, in a side view, a schematically illustrated apparatus 1 for the preparation of the electrochemical sensor 2. The apparatus comprises a housing 5 consisting of a housing upper part 5a and also of a housing lower part 5b, with the two housing parts 5a, 5b being mutually displaceably mounted in the direction of the displacement t. The housing lower part 5b has an opening 5m behind which a holding means 6 for the sensor 2 is arranged. In the housing upper part 5a there is disposed a means 7 for the dispensing of the electrolyte and also a means 8 for the dispensing of the membrane. These two means 7, 8 are coupled to an actuating means 5c in order to move the means 7, 8 in the direction of displacement s and thereby to supply the electrolyte 3 or the membrane 4 to the sensor 2 fixed in the holding means 6. The means 7, 8 are disposed in the interior of the housing 5.

FIG. 3 shows, in a longitudinal section, a sensor 2 which is held in the holding means 6 including an abutment part 6a, a first holding part 6b and also a lug 6c. The sensor 2 can be released from the holding means 6 in that the lug 6c is depressed and thereby the first holding part 6b released from the engagement in the sensor 2. It can prove advantageous to close the opening 5m shown in FIG. 2 with a second holding part 6d, with this holding part 6d being so designed that it lies on the sensor 2 and additionally fixes it.

FIG. 4 shows a longitudinal section through a means 7 for the dispensing of the electrolyte 3. The means 6 comprises a container 7d, filled with electrolyte 7e, which has a closure 7f (for example with a ball). The container 7d is mounted in an outlet and holding part 7a. The outlet and holding part 7a can be connected via a web 7c to a common carrier 11. A pressure exerted downwardly onto the actuating means 5c is transmitted via the cylinder-like projection 5d onto the means 7 so that this is first moved downwardly until the spacer 7b contacts the sensor head 2a. Thereafter the container 7d is pressed into the outlet and holding part 7a, with the closure 7f opening with a correspondingly high internal pressure and the electrolyte 7e flowing via the passage of the outlet and holding part 7a onto the surface of the sensor head 2a. As soon as the pressure is taken from the actuating means 5c the means 7 moves upwardly again and the spacers 7b no longer lie on the sensor head 2a.

FIG. 5 shows a longitudinal section through a means 8 for the dispensing of the membrane 4. The means 8 comprises a holder 8a with lugs 8b for the holding ring 4a of the membrane 4. The means 8 further includes a piston 8d which is displaceably mounted via the guide part 5e and which is coupled via a spring 8f to the movable housing upper part 5c and which has at the bottom a pressing body 8e with a contact pressure surface 8g which uniformly contacts the membrane 4. The means 8 can be connected via the holding part 8c to a common carrier 11. The pressure exerted downwardly onto the actuating means 5c acts via the cylindrical projections 5d onto the spring 8f so that the piston 8d is moved downwardly. During this movement the lugs 8b enter into contact with the sensor 2 and are thereby spread apart, so that the membrane 4 is released and thereafter secured to the sensor 2. During the mounting of the membrane 4 onto the sensor 2 a comparatively uniform areal force lies over the whole membrane 4, brought about by the pressing body 8e, so that the electrolyte 3 located between the sensor head 2a and the membrane 4 is uniformly displaced outwardly before the membrane 4 is fixedly connected via the holding means 4a to the sensor 2. The means 8 has the advantage that the maximum pressing force of the pressing body 8e is essentially determined by the spring 8f which has the consequence that the membrane 4 is connected to the sensor 2 preferably independently or hardly dependently on the force acting on the movable housing part 5c. The force brought about by the spring 8f is reproducible, which permits a uniform covering of the sensor 2 with the membrane 4. The sensor 2 has in particular a uniform reproducible layer thickness of electrolyte 3.

The apparatus shown in FIG. 2 could have the means 6, 7, 8 shown in the FIGS. 3, 4 and 5 in that the means 6 is arranged in the lower part 5b of the housing and the means 7 and 8 are arranged in the upper part 5a of the housing.

Figure 7:
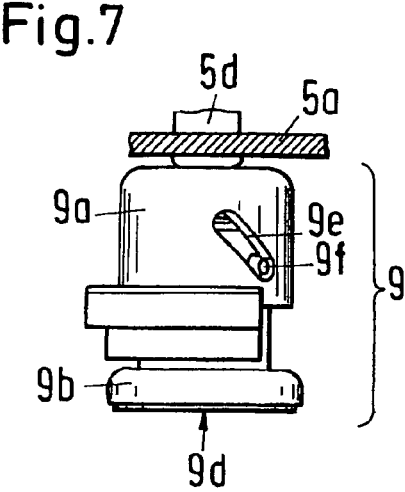
FIG. 7 a side view of the means for the cleaning of the sensor head.

FIG. 6 shows a longitudinal section through a means 9 for the cleaning of the sensor head 2a. The means 9 includes a holding part 9a in which a rotary piston 9b with a cleaning cloth 9d is displaceably mounted. The rotary piston 9b is moreover coupled via a spring 9c to the holding part 9a. A pressure exerted downwardly onto the actuating means 5c is transmitted via the cylinder-like projection 5d, which is guided in the housing upper part 5a, onto the means 9 so that the latter is moved downwardly. During this movement the cleaning cloth 9d contacts the sensor head 2a at some time so that the rotary piston 9b is thrust into the holding part 9a as a result of the further movement. The relative movement of the rotary piston 9b with respect to the holding part 9a causes, as can be seen in FIG. 7, a rotary movement of the rotary piston 9b. FIG. 7 shows in the side view the means 9 for the cleaning of the sensor head 2a. The holding part 9a has a slit 9e extending obliquely in which a cam 9f, which is fixedly connected to the rotary piston 9b, is displaceably mounted. If the cleaning cloth 9d now lies on the sensor head 2a and the holding part 9a is then moved further downwardly, then the rotary piston 9b will be thrust into the holding part 9a and the slit 9e and the cam 9f bring about a rotary movement of the rotary piston 9b and thus in particular of the cleaning cloth 9d, so that the sensor head 2a is particularly intensively cleaned.

Figure 8:
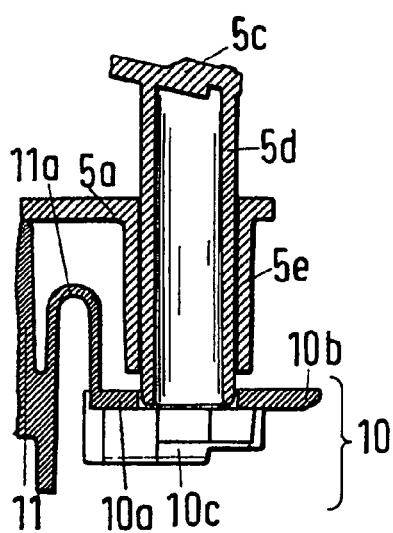
FIG. 8 a longitudinal section through a means for the removal of the membrane.

FIG. 8 shows a longitudinal section through a means 10 for the removal of the membrane 4 secured to a sensor 2. The means 10 includes a holding means 10a, a guide part 10b and also a lateral holding means 10c. The means 10 can be connected via a resilient connection means 11a to a common carrier 11. The sensor 2 with a membrane 4 is introduced into the means 10 with the membrane 4 aligned upwardly so that the holding ring 4a of the membrane 4 is held in the lateral holding means 10c. Thereafter, a force is exerted onto the membrane 4 via the actuating means 5c which is guided via the cylinder-like projection 5d in the housing upper part 5a and also by the guide part 5e. Through this force exerted by the projection 5d the holding ring 4a is separated from the sensor 2. During this separation the holding means 6 shown in FIG. 3 is preferably arranged beneath the means 10 so that the sensor 2 is held in the holding means 6 directly after the release of the holding ring 4a.

The means 6, 7, 8, 9, 10 shown in the FIGS. 3 to 8 all serve for the preparation of an electrochemical sensor 2. Preferably at least the means 6, 7 and 8 are arranged in one apparatus 1 for the preparation of the electrochemical sensor 2 as shown in FIG. 2. it can also prove advantageous to provide further means, such as the means 9 and 10. All these means 6, 7, 8, 9, 10 can be arranged in the most diverse manner in an apparatus 1 in order to enable a preparation of the sensor 2.

Figure 9:
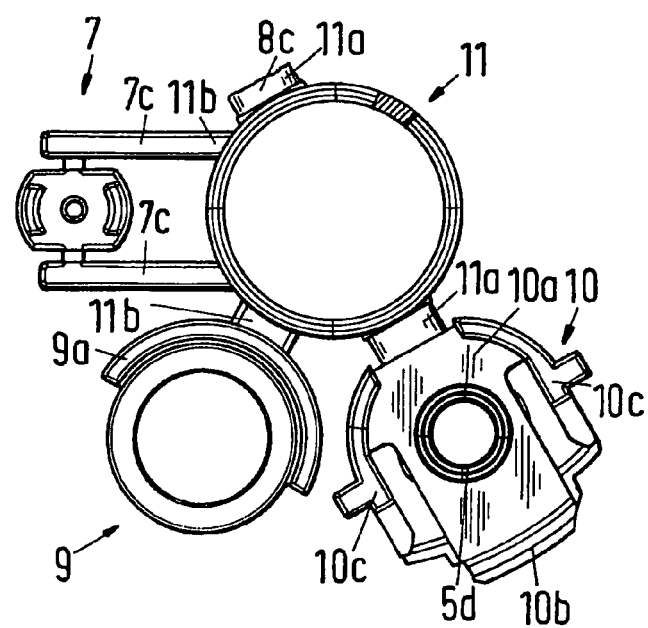
FIG. 9 a view onto a common carrier.

FIG. 9 shows a top view of a common carrier 11 on which the means 10 for the removal of the membrane 4, the means 9 for the cleaning of the sensor head 2a, the means 7 for the dispensing of the electrolyte 3 and also the means 8 for the dispensing of the membrane 4 are arranged distributed in the peripheral direction. Of the means 8 only the holding part 8c is shown.

Figure 13:
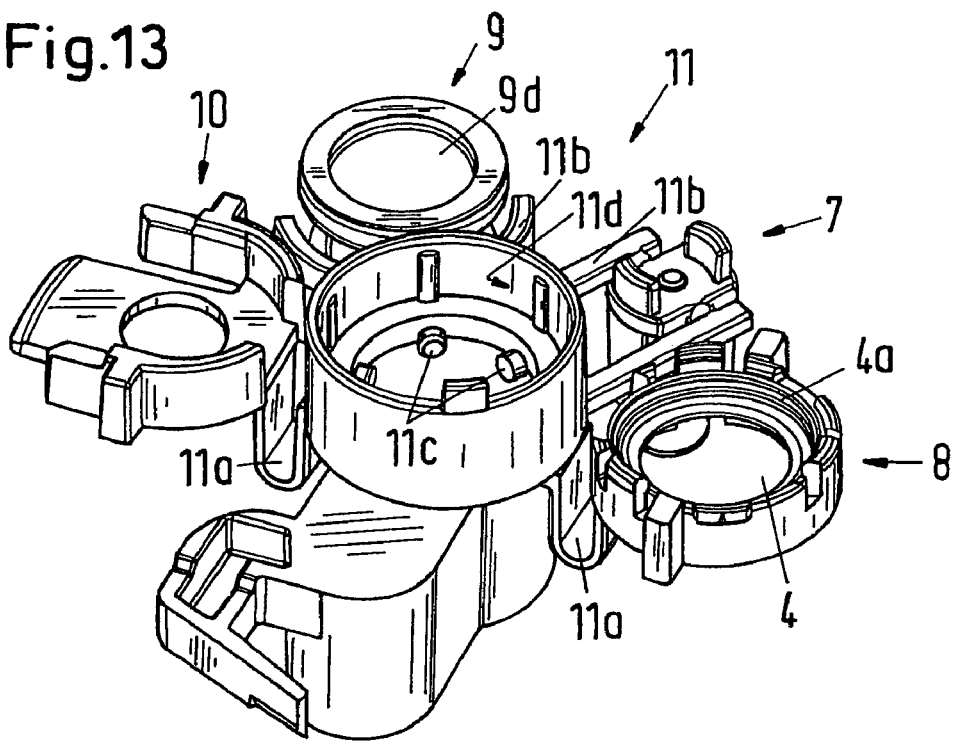
FIG. 13 a perspective view of the common carrier.
Figure 14:
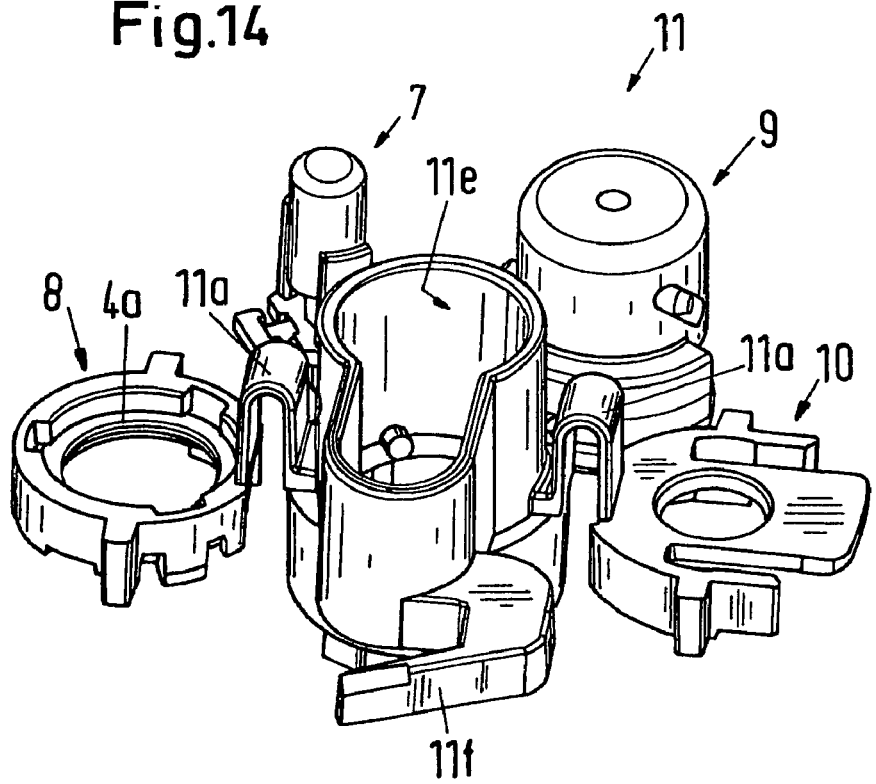
FIG. 14 a further perspective view of the common carrier.

FIG. 13 shows in a three-dimensional elevation a further embodiment of a common carrier 11 with means 10, 9, 7 and 8 arranged distributed in the peripheral direction. The transparent membrane 4 with the holding ring 4a is mounted in the means 8 for the dispensing of the membrane. The carrier 11 showing in FIG. 13 includes all consumed parts which are required for the preparation of the electrochemical sensor 2. The carrier 11 is preferably designed as a disposable part, i.e. as a throw-away part. FIG. 14 shows the carrier 11 shown in FIG. 13 in a view from below. The carrier 11 includes resilient connection means 11a with which the means 8 and 10 are connected together and also a rigid connection means 11b with which the means 7 and 9 are connected. The carrier 11 further includes a first connection part 11d, cams 11c, a second connection part 11e and also a locking part 11f.

Figure 10:
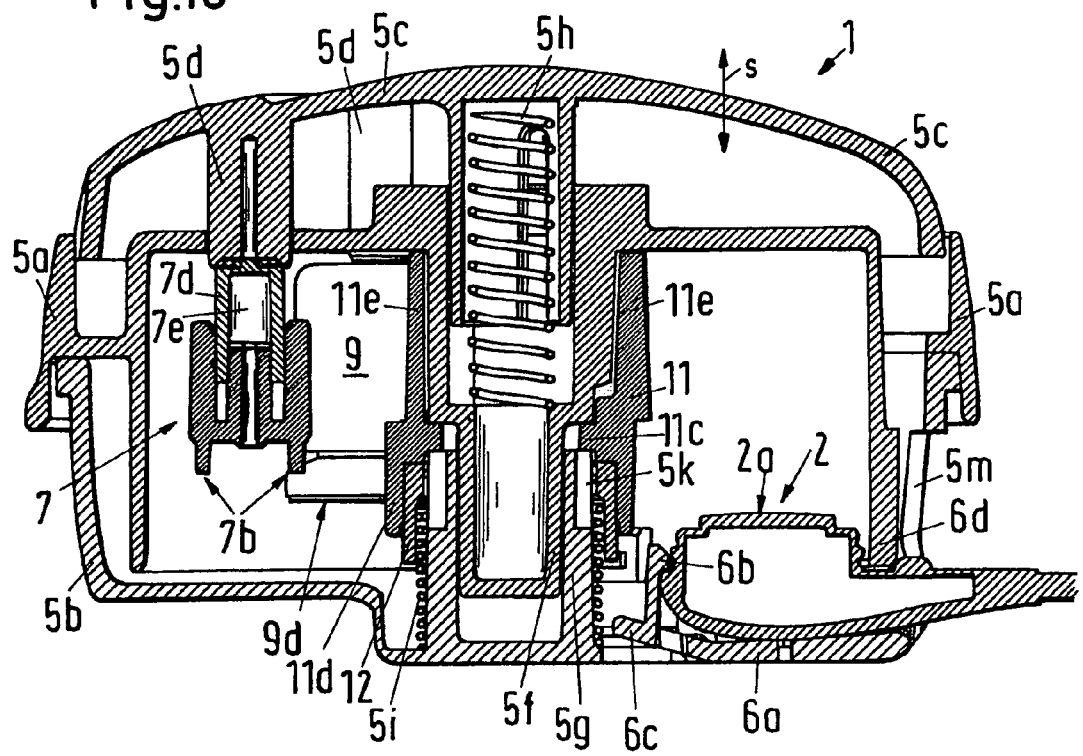
FIG. 10 a cross-section through an apparatus for the preparation of an electrochemical sensor.
Figure 11:
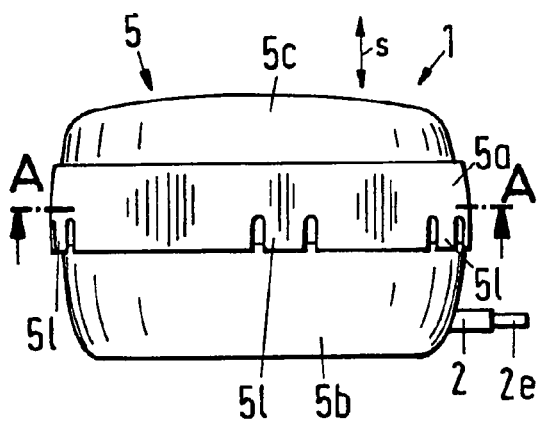
FIG. 11 a side view of the housing of the apparatus for the preparation of the sensor.
Figure 12:
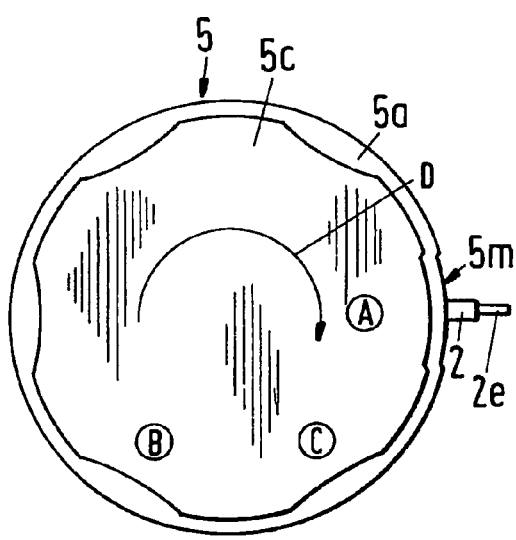
FIG. 12 a view onto the housing of the apparatus for the preparation of the sensor.

FIG. 10 shows, in a cross-section, a particularly advantageously designed apparatus 1 for the preparation of an electrochemical sensor 2. The same apparatus 1 is shown in FIG. 11 in a side view and in FIG. 12 in the plan view. As is shown in FIG. 11 the housing 5 includes a housing upper part 5a and also a housing lower part 5b which form two half shells within which the common carrier 11 and further components are arranged. The housing upper part 5a has a plurality of holding means 51 arranged distributed in the peripheral direction which engage into the housing lower part 5b in such a way that a bayonet connection is formed thanks to which the two housing parts 5a, 5b can be mutually connected and also released again. The bayonet connection is moreover designed in such a way, and the holding means 51 are distributed in the peripheral direction in such a way, that the two housing parts 5a, 5b are mutually rotatably mounted. The housing 5 also includes a movable housing upper part 5c also termed actuating means which is displaceably mounted with respect to the housing upper part 5a and also with respect to the housing lower part 5b in the direction of movement s. A part of the sensor 2 projects into the opening 5m and is located within the interior of the housing 5. The plan view of FIG. 12 likewise shows a housing 5 with the housing upper part 5a and also with the actuating means 5c which is displaceably mounted relative to the latter. The housing upper part 5a is moreover rotatably mounted, together with the actuating means 5c in the direction of rotation D, with respect to the housing lower part 5b. The actuating means 5c has markings A, B and C at the surface. If the marking A is in the opening 5m, then the sensor 2 can, as shown, be introduced into the apparatus 1. Thereafter the actuating means 5c is pressed downwardly in the direction of the movement s and thereafter relaxed upwardly again. Thereupon the housing upper part 5a with the actuating means 5c is turned in the direction of rotation D and the actuating means 5c is pressed downwardly again in the direction of movement s and relaxed upwardly again. This process is repeated until the marking B is located at the opening 5m. In this position of the actuating means 5c the preparation of the sensor 2 is completed and it can be removed from the apparatus 1. Through a further rotation of the actuating means 5c in the direction D the marking C reaches the opening 5m. In this position the bayonet connection is unlatched and the housing 5 can be opened. Thereafter the common carrier can be removed from the housing 5 and replaced by a new common carrier 11. The housing is put together again and the bayonet connection is latched so that the apparatus 1 is available for the preparation of a further sensor 2.

FIG. 10 shows the actuating means 5c which is displaceably mounted with respect to the housing upper part 5a in the direction of movement s, with a resetting spring 5h being located at the center in order to always bring the actuating means 5c back into the illustrated basic position again after a movement downwardly. The actuating means 5c includes a plurality of plungers 5d which are formed as cylindrical projections and which act on the means 7, 8, 9 or 10. The holding means 6 shown in FIG. 3, in which the sensor 2 can be firmly held, is arranged in the housing lower part 5b. The housing lower part 5b also includes a pivot bearing 5g in which a spigot 5f of the housing upper part 5a is rotatably mounted so that the housing upper part 5a is rotatably mounted with respect to the housing lower part 5b in the direction of rotation D. The common carrier 11 is arranged in the internal space of the housing 5. The common carrier 11 is connected via a first connecting part 11d with the rotatable bearing 12. The rotatable bearing 12 is pressed upwardly by a spring 5i. The carrier 11 is rotatably mounted with respect to the housing lower part 5b. The carrier 11 is moreover connected via a second eccentric connecting part 11e to the housing upper part 5a and coupled to the housing upper part 5a with respect to a rotation in the direction D. The pivot bearing 5g has at the outer side grooves 5k extending in the direction s into which the cams 11c engage during the movement in the direction s, so that the common carrier 11 and also the housing upper part 5a is blocked during this movement with respect to rotation in the direction D.

All the components illustrated in the FIGS. 3 to 8 are arranged in the apparatus 1 of FIG. 10, with only the apparatus 7 and 9 being explicitly shown for the sake of simplicity of the illustration in FIG. 10, whereas the apparatuses 8 and 10 are not shown. The carrier 11 arranged in FIG. 10 is however in principle identical to the carrier 11 shown in FIGS. 13 and 14 and thus includes the apparatuses 7, 8, 9 and 10.

The preparation of a electrochemical sensor 2 with the apparatus 1 partly shown in FIG. 10 includes the following steps:

The bayonet connection of the two housing halves 5a, 5b is opened, the common carrier 11 is removed, a new common carrier 11, such as is shown in the FIGS. 13 and 14 is inserted, the bayonet connection of the two housing halves 5a, 5b is closed again and the marking A of the actuating means 5c turned to the opening 5m.

The sensor 2 shown in FIG. 1b comprising a membrane 4 is introduced into the inlet opening 5m of the housing 5, with the means 10 shown in FIG. 8 for the removal of the membrane 4 being located behind the inlet opening 5m. As soon as the sensor 2 is introduced into the means 10 the actuating means 5c is pressed downwardly so that the cylinder-like projection 5d releases the sensor 2 from the holding ring 4a and the sensor 2 is supplied to the holding means 6 as shown in FIG. 10. The holding ring 4a with the membrane 4 remains in the means 10. Thereupon the pressure on the actuating means 5c is reduced or the actuating means 5c is fully released so that the actuating means 5c moves upwardly again into the base position shown in FIG. 10.

Thereupon the housing cover 5a is rotated in the direction D until the means 9 for the cleaning of the sensor head 2a is located above the sensor 2. The actuating means 5c is then pressed downwardly and the sensor head 2a is cleaned, as already described with respect to FIGS. 6 and 7, so that any electrolyte eventually present on the sensor head 2a is removed. The actuating means 5c is thereupon released again so that it moves upwardly.

Thereupon the housing cover 5a is turned in the direction D until the means 7 for the dispensing of the electrolyte is located over the sensor 2. The actuating means 5c is then pressed downwardly and the sensor head 2a is provided with electrolyte 3 as already described with respect to FIG. 4. Thereafter the actuating means 5c is released again so that it moves upwardly.

Thereupon the housing cover 5a is turned in the direction D until the means 8 for the dispensing of the membrane 4 is located above the sensor 2. The actuating means 5c is then pressed downwardly and the membrane 4 is connected to the sensor 2 as already described with the FIG. 5. Thereafter the actuating means 5c is released again so that it moves upwardly.

Thereupon the housing cover 5a is turned in the direction D until the marking B is located in front of the opening 5m so that the now completely prepared sensor 2 can be removed from the apparatus 1 by renewed pressing and releasing of the housing cover 5a.

The housing cover 5a is then turned further, until the marking C is located in front of the opening 5m. The bayonet connection of the two housing halves 5a, 5b is thus unlocked, the common carrier 11 can be removed, a new common carrier 11, as is shown in FIGS. 13 and 14 can be inserted and the bayonet connection of the two housing halves 5a, 5b can be closed again.

The apparatus 1 is now ready to prepare a further electrochemical sensor 2.

In order to position the respective means 7, 8, 9, 10 precisely with respect to the sensor 2 held in the holding means 6 during rotation of the housing cover 5a the housing lower part 5b has, as illustrated in FIG. 15 in a section A-A along the FIG. 11, inwardly projecting cams 5n on which the locking part 11f of the common carrier 11 respectively abuts with its tongue 11g. The cams 5n are arranged distributed in the peripheral direction so that, on abutment of the locking part 11f, the respective means 7, 8, 9, 10 is arranged precisely with respect to the sensor 2 so that the function corresponding to means 7, 8, 9, 10 can be executed at the sensor 2 by a downward pressing the actuating means 5c. The tongue 11g of the locking part 11f is designed in such a way that it comes to lie directly after the cam 5n while the common carrier 11, after completely moving downwardly, moves upwardly again and is thus no longer in engagement with the cam 5n. Thus the housing cover 5a is again freely rotatably in the direction of rotation D until the locking part 11f engages into the next projecting cam 5n. This design causes the actuation of the apparatus 1 to be compulsorily guided in that the operation which has to take place for each step is preset. The housing cover 5a is rotated in the direction of rotation D up to an abutment. Thereafter a movement of the actuating means 5c, and associated with it a movement of common carrier 11 must necessarily take place in the direction s. After the housing 5 is again located in the basic position shown in FIG. 10 the cover 5a can again be turned in the direction of rotation D up to the next following abutment This compulsory guidance ensures that during the preparation of the sensor 2 no operation is forgotten. The apparatus 1 is thus particularly suited for use in an environment with high stress, for example at an intensive care station or for a patient at home who hardly has experience with the preparation of an electrochemical sensor 2.

The embodiments of apparatuses for preparing an electrochemical sensor 2 shown in the Figures represent embodiments from a plurality of design possibilities in order to satisfy the required function of the preparation of the sensor 2.

The apparatus 1 shown in FIG. 10 is also suitable to cover a sensor 2 with a membrane 4 for the first time. The sensor 2 without membrane 4 and holding ring 4a is introduced for this purpose in the housing position shown in FIG. 12 into the inlet opening 5m of the housing 5 and, by pressing the actuating means 5c downwardly secured in the holding means 6 with the aid of the means 10. Thereafter, the apparatus is actuated further, as described in FIG. 10, so that the sensor 2 is provided with electrolyte and membrane. As soon as the housing upper part 5a and also the actuating means 5c have been turned sufficiently far that the marking B is located at the inlet opening 5m the sensor 2 is fully prepared.

The means 7, 8, 9, 10 may not all be arranged at the common carrier 11 but can rather also be connected individually or in groups directly to the housing 5.

In the above it has been described several times that the actuating means 5c is pressed in the direction downwardly with respect to the illustrated arrangement of the apparatus 1. The apparatus 1 can also be fully held in the hand so that the actuating means 5c is pressed downwardly with respect to the housing lower part 5b. The term downwardly not only means a vertical direction with respect to the surface of the earth, but also a movement towards the housing lower part 5b.

The invention claimed is:

1. Handheld apparatus for the preparation of an electrochemical sensor comprising a sensor head in order to provide the sensor head with an electrolyte and a membrane, the apparatus comprising a holder for the sensor, a dispenser for the electrolyte, a dispenser for the membrane and a common carrier, wherein:

the holder, the dispenser for the electrolyte, the dispenser for the membrane and the common carrier are arranged within a common housing that is able to be handheld with the common housing comprising a housing upper part and a housing lower part being mutually rotatably mounted in a direction of rotation, the housing upper part being capable of being moved by hand in the direction of rotation, the housing upper part and the housing lower part each comprising a half shell which form a common inner space for the reception of at least the dispenser for the electrolyte, the dispenser for the membrane, the common carrier and the holder for the sensor;

the holder is fixedly arranged in said housing lower part, with the housing lower part comprising an opening where the opening leads to the holder to engage the electrochemical sensor;

the housing upper part further comprising an actuator which is displaceably mounted essentially in the vertical direction with respect to the housing upper part and the housing lower part; and the dispenser for the electrolyte and the dispenser for the membrane are arranged within the common carrier within said common housing, the common carrier has an operative connection to the housing upper part in order to rotate the common carrier in the direction of rotation if the housing upper part is rotated in the direction of rotation, the common carrier, comprising the dispenser for the electrolyte and the dispenser for the membrane, is rotatably mounted in the housing lower part in said direction of rotation in order to position the dispenser for the electrolyte and the dispenser for the membrane in sequence with respect to the sensor held in the holder by manually moving the housing upper part in the direction of rotation, and to supply the electrolyte and membrane to the sensor by manually moving the actuator in said vertical direction by downward pressing exerted onto the actuator with the actuator comprising a plurality of plungers capable of either linear or rotational movement in connection with the actuator, wherein:

a first plunger releases electrolyte from a container opened by pressure exerted on the actuator so that electrolyte is applied to the sensor head; and a second plunger by pressure exerted downwardly on the actuator releases the membrane with a pressing surface that reproducibly displaces the electrolyte.

2. Handheld apparatus in accordance with claim 1, wherein the common carrier is insertable within said common housing.

3. Handheld apparatus in accordance with claim 1, wherein the dispenser for the membrane is to dispense the membrane such that the membrane is able to be secured to the sensor head with a reproducible pressing force.

4. Handheld apparatus in accordance with claim 3, wherein the dispenser for the membrane includes at least a pressing body including at least a pressing surface, wherein the pressing body is arranged such that the pressing surface contacts the membrane during the dispensing of the membrane in order to displace electrolyte located between the membrane and the sensor head in such a way that the sensor connected to the membrane has a reproducible layer thickness of the electrolyte, between the sensor head and the membrane.

5. Handheld apparatus in accordance with claim 4 comprising an element for cleaning the sensor head wherein the element for cleaning the sensor head is displaceably mounted with respect to the holder, and wherein the element for cleaning the sensor head is able to be so positioned with respect to the holder so that the element for cleaning mechanically cleans the sensor head of the sensor held in the holder.

6. Handheld apparatus in accordance with claim 1, comprising an element for the removal of a membrane, the element for the removal of a membrane being displaceably mounted with respect to the holder, and wherein the element for the removal of the membrane is able to be positioned with respect to the holder such that after the removal of a used membrane the sensor is able to be supplied to the holder.

7. Handheld apparatus in accordance with claim 1, wherein at least the dispenser for the electrolyte and the dispenser for the membrane are secured to a common carrier, and wherein the element for the cleaning and the element for the removal of the membrane are secured to the common carrier.

8. Handheld apparatus in accordance with claim 1, wherein the housing lower part and the housing upper part are each designed as a half shell which form a common inner space for the reception of at least the dispenser for the electrolyte, the dispenser for the membrane, an element for the cleaning of the sensor head and an element for the removal of a membrane.

9. Handheld apparatus in accordance with claim 8 wherein the housing lower part and the housing upper part are releasably connectable to one another.

10. Handheld apparatus in accordance with claim 8, wherein the actuator has an operative connection to at least one of the dispenser for the electrolyte, the dispenser for the membrane, the element for the cleaning of the sensor head and the element for the removal of a membrane in order to bring about a force and/or a movement on at least one of the dispenser for the electrolyte, the dispenser for the membrane, the element for the cleaning of the sensor head and the element for the removal of a membrane via the actuator.

11. Handheld apparatus in accordance with claim 7, wherein the common carrier is formed as an exchangeable part.

12. A common carrier for the handheld apparatus in accordance with claim 1, comprising at least one container filled with electrolyte and a membrane.

13. The common carrier in accordance with claim 12, comprising an element for cleaning the sensor head and an element for the removal of the membrane.

14. The common carrier in accordance with claim 12, comprising a first connection part which defines an axis of rotation and wherein the container and the membrane are arranged spaced apart in a peripheral direction with respect to the axis of rotation.

15. The common carrier in accordance with claim 14 wherein the element for the removal of the membrane, the element for cleaning the sensor head, the dispenser for the electrolyte and the dispenser for the membrane are arranged following one another in the peripheral direction.

16. A method for the manual preparation of an electrochemical sensor with a handheld apparatus to provide a sensor head of said sensor with an electrolyte and a membrane, said handheld apparatus comprising a common housing that is able to be handheld, with the housing comprising a housing upper part and a common housing lower part rotatably coupled, an actuator manually accessible comprising at least a first and second plunger, capable of linear movement in a vertical direction with respect to the housing upper part and the housing lower part, in connection with the actuator, a holder and a common carrier comprising at least a dispenser for the electrolyte and a dispenser for the membrane, the method comprising:
securing said sensor in the holder by moving the sensor through an opening in the housing lower part, wherein the holder is fixedly arranged with respect to said housing lower part and wherein the dispenser for the electrolyte and the dispenser for the membrane are rotatably mounted with respect to the holder;
manually moving the common carrier by movement of the housing upper part in a direction of rotation in relation to the housing lower part to position the dispenser for the electrolyte above the sensor head;
applying a first force by downward pressing exerted onto said actuator to move the first and second plunger in said vertical direction, wherein on application of the first downward pressing force the dispenser for the electrolyte gets in contact with the sensor head, and wherein further movement of the first plunger in said vertical direction releases the electrolyte from a container opened by pressure exerted by said first plunger and said sensor head;
releasing the first force onto said actuator and moving the actuator opposite to said vertical direction, manually moving the common carrier to position the dispenser for the membrane above the sensor head; and
applying a second force by downward pressing exerted onto said actuator to move the first and second plunger in said vertical direction, wherein on application of the second downward pressing force said dispenser for the membrane gets in contact with the sensor head to supply the membrane to the sensor head, wherein the second plunger by pressure exerted in said vertical direction on the actuator releases the membrane with a pressing surface that reproducibly displaces the electrolyte, the said applying of the force moves the second plunger in said vertical direction.

17. The method in accordance with claim 16, wherein the membrane is supplied to the sensor head with a reproducible pressing force defined by a spring in order to reproducibly displace electrolyte present between the membrane and the sensor head in such a way that in each case a reproducible layer thickness of electrolyte arises between the membrane and the sensor head.

18. The method in accordance with claim 16, comprising removing a original membrane from the sensor head, cleaning the sensor head, supplying the electrolyte to the sensor head supplying the membrane to the sensor head, all in a compulsory guided manner.

19. The method in accordance with claim 18, wherein the compulsory guided manner takes place in such a way that the sensor is secured within the common housing and that individual steps at the sensor are compulsorily guided by rotation of a part of the common housing.

20. Handheld apparatus in accordance with claim 1, wherein the dispenser for the membrane includes at least a pressing body including at least a pressing surface, wherein the pressing body is arranged such that the pressing surface contacts the membrane through movement of the second plunger directed by hand force applied on the actuator during the dispensing of the membrane in order to displace electrolyte located between the membrane and the sensor head in such a way that the sensor connected to the membrane has a reproducible layer thickness of the electrolyte, and has a uniform layer thickness of the electrolyte, between the sensor head and the membrane.

21. Handheld apparatus in accordance with claim 8 wherein the housing upper part and the housing lower part are releasably connectable to one another by a mutual rotary movement.

22. Handheld apparatus in accordance with claim 6, wherein the common carrier is formed as a disposable part.

23. The common carrier in accordance with claim 12 comprising a first connection part which defines an axis of rotation wherein the container, the membrane, an element for cleaning and an element for the removal of the membrane are arranged spaced apart in a peripheral direction with respect to the axis of rotation.

* * * * *